US00PP21068P2

(12) United States Plant Patent

Kristensen

(10) Patent No.: US PP21,068 P2

(45) Date of Patent: Jun. 15, 2010

(54) *OSTEOSPERMUM* PLANT NAMED 'SAKOST3442'

(50) Latin Name: *Osteospermum hybrida*
Varietal Denomination: 'SAKOST3442'

(75) Inventor: Niels G. Kristensen, Grauballe (DK)

(73) Assignee: Sakata Ornamentals Europe A/S, Marslev (DK)

( * ) Notice: Subject to any disclaimer, the term of this patent is extended or adjusted under 35 U.S.C. 154(b) by 0 days.

(21) Appl. No.: 12/383,877

(22) Filed: Mar. 30, 2009

(51) Int. Cl.
*A01H 5/00* (2006.01)

(52) U.S. Cl. ..... Plt./360

(58) Field of Classification Search ..... Plt./360
See application file for complete search history.

*Primary Examiner*—Annette H Para
(74) *Attorney, Agent, or Firm*—Jondle & Associates, P.C.

(57) ABSTRACT

A new *Osteospermum* plant particularly distinguished by having flowers with a white ray floret color and blue disc florets, medium flower size, flowers that stay open under low light conditions and mounded cascading plant habit, is disclosed.

1 Drawing Sheet

Genus and species:
*Osteospermum hybrida.*
Variety denomination: 'SAKOST3442'.

BACKGROUND OF THE NEW PLANT

The present invention comprises a new and distinct cultivar of *Osteospermum*, botanically known as *Osteospermum hybrida*, and hereinafter referred to by the cultivar name SAKOST3442'. SAKOST3442' originated from a hybridization of proprietary hybrid *Osteospermum* breeding lines '98071' and '98064' in Aabyhoej, Denmark. The proprietary female parent, '98071' (unpatented) has a white flower color and a cascading plant habit. The proprietary male parent, '98064' (unpatented) has a dark pink flower color and a compact and semi-cascading plant habit.

In May 2001, the two *Osteospermum* lines '98071' and '98064' were crossed and seeds were obtained. The seeds were sown and 300 plants were grown in pots for evaluation. Out of 300 $F_1$ lines, plant number 27 which has a white ray floret color with blue disc florets and a mounded cascading plant habit was selected.

In February 2002, plant number 27 was vegetatively propagated by cuttings and re-evaluated in an open field and a greenhouse. Plant number 27 was given the breeder code number '202187' and the stability of the distinct characteristics of this variety was confirmed.

In spring 2005, plants were evaluated again in pots and in an open field The selection was named 'SAKOST3442' and was found to reproduce true to type in successive generations of asexual propagation.

SUMMARY OF THE INVENTION

The following are the most outstanding and distinguishing characteristics of this new cultivar when grown under normal horticultural practices in Salinas, California.

1. White ray floret color with blue disc florets
2. Medium flower size;
3. Flowers that stay open under low light conditions; and
4. Mounded, cascading growth habit.

DESCRIPTION OF PHOTOGRAPHS

This new *Osteospermum* plant is illustrated by the accompanying photographs which show the plant's overall plant habit including form, foliage and flowers. The photographs are of a plant grown four and a half months from transplant date and five and a half months from stick date into 8-inch pots from rooted cuttings in Salinas, Calif. in the spring of 2008. The colors shown are as true as can be reasonably obtained by conventional photographic procedures.

DESCRIPTION OF THE NEW CULTIVAR

Figure 1:
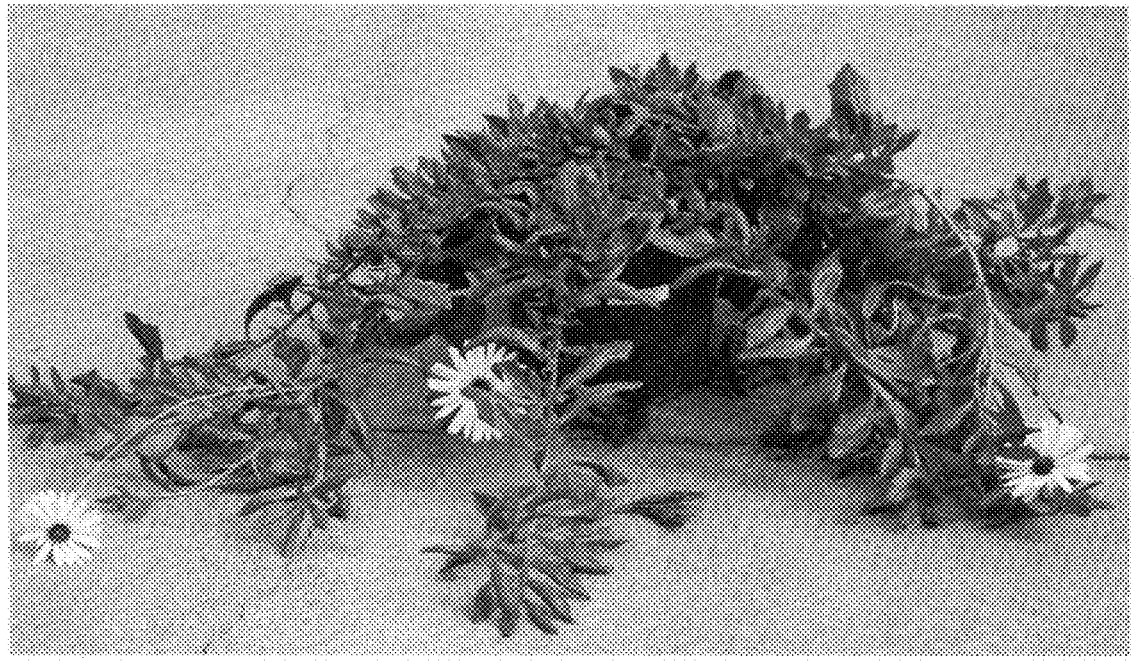
FIG. 1 shows overall plant habit of the plant grown in a pot.
Figure 2:
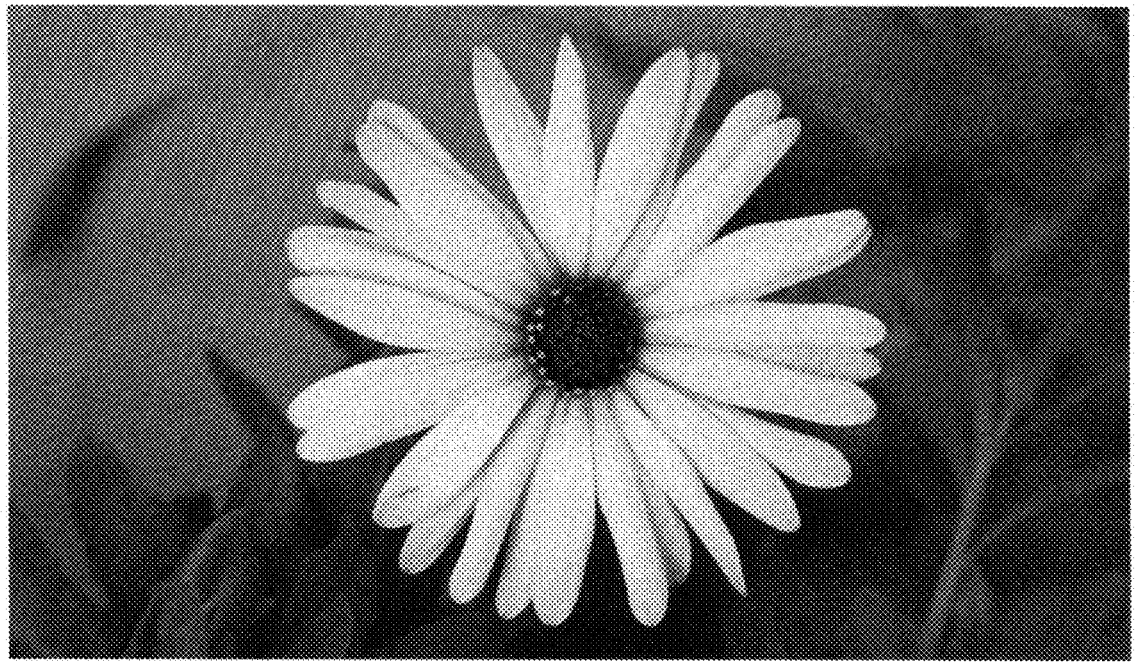
FIG. 2 shows the mature inflorescence of the plant.

The following detailed descriptions set forth the distinctive characteristics of 'SAKOST3442'. The data which define these characteristics were collected from asexual reproductions carried out in Salinas, Calif. Data was collected on plants grown approximately four and a half months from transplant date and five and a half months from stick date into 8-inch pots under greenhouse conditions in Salinas, California in the spring of 2008. Color references are to the RHS Colour Chart of The Royal Horticultural Society of London (RHS), $4^{th}$ edition.

DESCRIPTION OF THE NEW PLANT

Classification:

*Family.*—Compositae.

*Botanical.*—*Osteospermum* hybrida.

*Common.*—*Osteospermum*, Cape Daisy, South African Daisy.

Parentage:

*Female parent.*—A hybrid proprietary *Osteospermum* line '98071', having a white flower color and a cascading plant habit (unpatented).

*Male parent.*—A hybrid proprietary *Osteospermum* line '98064', having a dark pink flower color and a compact and semi-cascading plant habit (unpatented).

Growth:

*Time to produce a rooted cutting.*—Cuttings will colonize a 2.5 cm diameter by 2.5 cm tall greenhouse tray cell with peat-based plant media in approximately four weeks. Cuttings are dipped in a normal dilution (1:9) of Dip 'N Grow root-inducing solution in water. The trays are misted hourly during rooting.

*Environmental conditions for plant growth.*—Rooted cuttings are transplanted to pots with a 16 cm diameter, one plant per pot. Peat-based growing media is used. The pots are watered using a 150-200 ppm fertilizer solution using 18-8-18 fertilizer. The soil is allowed to dry between watering. During the first few weeks after transplanting the plants should have evening temperatures around 15° -18° C. for good root growth. When plants reach 7.5-10 cm in height they are pinched back to 5-6 leaves to promote branching. Spring and summer daytime high temperatures in Salinas, Calif., where the data was collected, range from 16° -25° C.

*Time to bloom from propagation.*—Approximately four weeks when rooted vegetative cuttings are transferred to a 5-inch diameter pot. Flowering season is all year in the United States. Vernalization is not required to induce flowering.

Plant description:

*Habit.*—Trailing, cascading.
*Life cycle.*—Perennial.
*Form.*—Spreading, branching.
*Height* (*from soil line to first node*).—2.0 cm.
*Height* (*from soil line to top of foliage*).—12.0 cm.
*Width.*—90.0 cm.

Stems:

*General.*—Few.
*Shape.*—Circular in cross section.
*Stem length* (*total*).—15.0 cm.
*Diameter.*—0.4 cm.
*Internode length.*—2.0 cm.
*Color.*—RHS 144A (Yellow-green) and RSH 187A (Greyed-purple).
*Pubescence.*—Absent.
*Anthocyanin color.*—Very slight, RHS N187A (Greyed-purple).

Branches:

*General.*—Circular in cross section.
*Number of main branches.*—1.
*Total number of branches.*—12.
*Length.*—40.0 cm, approximately 2.0 cm from soil line to first node, 2.0 cm between first and second nodes.
*Diameter.*—0.5 cm.
*Internode length.*—4.0 cm.
*Color.*—RHS 144A (Yellow-green) and RSH 187A (Greyed-purple).
*Anthocyanin color.*—RHS 187A (Greyed-purple).
*Pubescence.*—Absent.

Leaves:

*Arrangement*—Alternate.
*Shape.*—Oblanceolate, curled.
*Apex.*—Acute.
*Base.*—Attenuate.
*Margin.*—Serrate.
*Venation.*—Pinnate.
*Surface* (*both surfaces*).—Dull.
*Surface pubescence* (*both surfaces*).—Very slight, mainly around edge.
*Pubescence color.*—RHS N155A (White).
*Attachment.*—Decurrant.
*Length.*—9.0 cm.
*Width.*—3.5 cm.
*Thickness.*—Less than 0.1 cm.
*Color.*—Upper surface: RHS 137A (Green) Lower surface: RHS 137C (Green).
*Venation color.*—Upper surface: RHS 143A (Green) Lower surface: RHS 143B (Green).

Inflorescence:

*Number per plant.*—3.
*Type.*—Capitulum (head); disc florets are perfect and ray florets are carpellate.
*Flowering habit.*—Determinate.
*Lastingness of flowers.*—3 to 4 days.
*Fragrance.*—None.
*Seed production.*—None.
*Diameter.*—8.0 cm.
*Depth.*—0.5 cm.
*Petal number.*—30 per inflorescence.
*Disc diameter.*—1.5 cm.
*Disc floret number.*—120 to 140 per inflorescence.
*Peduncle length.*—9.0 cm from inflorescence to first node.
*Peduncle diameter.*—0.3 cm.
*Peduncle color.*—RHS 143C (Green).
*Peduncle texture.*—Dull, very slight pubescence.
*Phyllaries.*—Arrangement: 22 per inflorescence, free, arranged symmetrically Length: 1.2 cm Width: 0.2 cm Apex: Acute Margin: Entire Shape: Linear, acute Color (Both surfaces): RHS 141A (Green).

Ray florets (ligules):

*Corolla.*—One petal per ray floret; only the outer row of florets are the ray florets.
*Number of ray florets per inflorescence.*—30.
*Length.*—3.0 cm.
*Width.*—0.8 cm.
*Shape.*—Lanceolate.
*Apex.*—Acute.
*Margin.*—Entire.
*Color.*—Upper surface: RHS N155A (White) with RHS 77B (Purple) at base Lower surface: RHS 76D (Purple) with RHS N77D (Purple) streaks.
*Pubescence.*—Glabrous.

Disc florets:

*Bud Color.*—RHS 93A (Violet-blue).
*Shape.*—Tubular.
*Apex.*—Pointed.
*Surface.*—Dull, pubescent.
*Size.*—Length: 0.6 cm Width: 0.1 cm.

Reproductive organs:

*Ovary.*—Superior in ray florets.
*Pistil form.*—One style with two stigma branches in ray florets.
*Pistil length.*—0.2 cm in ray florets.
*Stigma color.*—RHS 187A (Greyed-purple) at tip of branches and RHS 155A (White) at center to base in ray florets.
*Style color.*—RHS 155A (White) in ray florets
*Ovary.*—Superior in disc florets.
*Pistil form.*—One style with two stigma branches in disc florets.
*Stamens.*—5, fused into a single tube in disc florets.
*Anther color.*—RHS 187A (Greyed-purple) in disc florets.
*Pollen color.*—RHS 13A (Yellow) in disc florets.
*Filament color.*—RHS 155A (White) in disc florets.

Disease and insect resistance: Very disease resistant, however, plants are susceptible to aphids, thrips, whiteflies and worms.

COMPARISON WITH PARENTAL LINES AND KNOWN CULTIVARS

'SAKOST3442' is a distinct variety of *Osteospermum* owing to its white and purple flower color and mounded, cascading growth habit. 'SAKOST3442' is distinguished from its parents primarily by its white and purple flower color and mounded, cascading growth habit, as described in Table 1 (color references are to The Royal Horticultural Society Colour Chart, 4$^{th}$ edition):

TABLE I

Comparison with Parental Lines

| Characteristic | 'SAKOST3442' | Male Parent '98064' | Female Parent '98071' |
|---|---|---|---|
| Ray floret (ligule) color, upper surface: | RHS N155A (White) with RHS 77B (Purple) at base. | Dark Pink | White |
| Plant growth habit | Mounded cascading | Compact and semi-cascading | Cascading |

'SAKOST3442' is a distinct variety of *Osteospermum* owing to its unique white ray floret color with blue disc florets, medium flower size, flowers that stay open under low light conditions and mounded cascading plant habit. 'SAKOST3442' is most similar to the *Osteospermum* plant named 'Cape Daisy Nairobi Improved' or 'Aknar' (U.S. Plant Pat. No. 15,654); however, there are differences as described in Table 2 (color references are to The Royal Horticultural Society Colour Chart, 4$^{th}$ edition):

TABLE 2

Comparison with Similar Variety

| Characteristic | 'SAKOST3442' | 'Aknai' |
|---|---|---|
| Ray floret (ligule) color, upper surface: | RHS Ni 55A (White) with RHS 77B (Purple) at base. | RHS 1 55D (White) |
| Ray floret (ligule) color, lower surface: | RHS 76D (Purple) with RHS N77D (Purple) streaks. | RHS 1 57A (Green-White) with alternating longitudinal stripes of RHS 188B (Greyed-Green) and RHS 146C (Yellow Green) |
| Color of disc florets | RHS 93A (Violet-Blue) | RHS 97B (Violet-Blue) at apex, RHS 1 55A (White) at mid-section and RHS 157A (Green-White) at base. |
| Plant growth habit | Mounded cascading | Uniformly mounded |

I claim:

1. A new and distinct cultivar of *Osteospermum* plant as shown and described herein.

* * * * *